United States Patent [19]

Schmand et al.

[11] 4,233,456
[45] Nov. 11, 1980

[54] PROCESS FOR THE MANUFACTURE OF OPTICALLY ACTIVE, OPTIONALLY SUBSTITUTED 2-AMINO-2-PHENYLACETIC ACID

[75] Inventors: Horst Schmand, Bad Nenndorf; Wolfgang Dannenberg, Wunstorf, both of Fed. Rep. of Germany

[73] Assignee: Riedel-de Haen Aktiengesellschaft, Seelze, Fed. Rep. of Germany

[21] Appl. No.: 937,093

[22] Filed: Aug. 28, 1978

[30] Foreign Application Priority Data

Aug. 30, 1977 [DE] Fed. Rep. of Germany ....... 2738934

[51] Int. Cl.³ ............................................. C07B 19/00
[52] U.S. Cl. .................................. 562/401; 562/443; 562/444; 562/449; 260/465 E
[58] Field of Search ................ 562/443, 444, 449, 401

[56] References Cited

U.S. PATENT DOCUMENTS

| | | | |
|---|---|---|---|
| 3,385,852 | 5/1968 | Casadio | 562/443 X |
| 3,422,132 | 1/1969 | Fuchs | 562/443 X |
| 3,536,726 | 10/1970 | Fink et al. | 562/443 X |
| 3,808,254 | 4/1974 | Matthews | 562/443 X |
| 3,832,388 | 8/1974 | Lorenz | 562/401 |
| 3,887,606 | 6/1975 | Phillipps et al. | 562/401 |
| 3,976,680 | 8/1976 | Clark et al. | 562/443 X |
| 4,072,698 | 2/1978 | Hylton et al. | 562/443 X |
| 4,093,653 | 6/1978 | Boesten | 260/558 A |

OTHER PUBLICATIONS

Houben–Weyl, Methoden Der Organischen Chemie, 4th Ed., vol. IV/2, pp. 511–513, Georg Thieme Verlag, Stuttgart, (1955).

*Primary Examiner*—Natalie Trousof
*Assistant Examiner*—Vera C. Clarke
*Attorney, Agent, or Firm*—Curtis, Morris & Safford

[57] ABSTRACT

Optically active 2-amino-2-phenylacetic acid of the formula

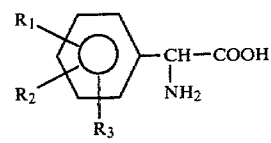

in which $R_1$, $R_2$ and $R_3$, which are identical or different, denote hydrogen, halogen, hydroxy, alkyl, acyl, or alkoxy, is prepared by asymmetrical transformation of a corresponding DL-aminophenylacetonitrile with L(+)-tartaric acid. To this end the corresponding DL-2-amino-2-phenyl-acetonitrile is reacted with approximately equimolar amounts of L(+)-tartaric acid in the presence of at least one alkanol having from 1 to 5 carbon atoms and/or at least one carbonyl compound at a temperature of from 0° to 50° C. and the mixture is stirred for 2 to 120 hours at the indicated temperature. The crystallized transformation product is separated, hydrolyzed by treatment with an acid and the desired product is isolated.

9 Claims, No Drawings

PROCESS FOR THE MANUFACTURE OF OPTICALLY ACTIVE, OPTIONALLY SUBSTITUTED 2-AMINO-2-PHENYLACETIC ACID

This invention relates to a process for the manufacture of optically active, optionally substituted 2-amino-2-phenylacetic acid by asymmetrical transformation of a corresponding DL-aminophenyl-acetonitrile with L(+)-tartaric acid.

It is the object of the present invention to provide a process for the manufacture of optically active compounds of the formula I (C-phenylglycines)

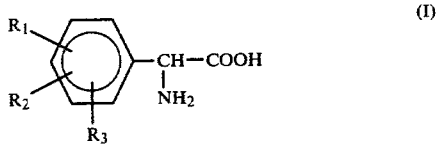

in which $R_1$, $R_2$ and $R_3$, which are identical or different, denote hydrogen, halogen, hydroxy, alkyl, acyl or alkoxy.

Optically active compounds of this type are known and represent, inter alia, important starting products for the manufacture of semi-synthetic β-lactam-antibiotics, for example ampicillin.

Various methods have been proposed to manufacture compounds of this type, especially optically active-2-amino-2-phenylacetic acid (phenylglycine), for example:

(1) The direct optical separation:

Phenylglycine reacts as a betaine and, therefore, attempts have been made to bring about salt formation with an optically active compound either via the amino group or via the acid group as a prerequisite for an optical separation.

Salt formation at the amino group is only possible with a very strong, optically active acid, for example camphor-10-sulfonic acid. In this reaction a yield of only 41% of D(−)phenylglyciine is obtained, calculated on DL-phenylglycine (cf. Japanese published specification 76,95,036). Moreover, the undesired L(+)stereomer must be racemized under severe conditions.

On the other hand, attempts have been made to block the amino group, for example by N-acetyl substitution and then to bring about salt formation with an optically active base. Apart from the fact that in this manner yields of only 16% of D(−)phenylglycine, calculated on DL-phenylglycine are obtained, it is a drawback that the optically active bases are very expensive (CS-PS 121,645 according to CA review 68, 22254 s (1968)).

Furthermore, experiments have been carried out to prepare optically active phenylglycidine by inoculating a salt solution with an enantiomer and subsequently selectively crystallizing. But owing to the weak effect, it is not possible to operate in batches and continuous processes require a high expenditure of apparatus equipped with control engineering (cf. U.S. Pat. No. 3,933,902).

(2) The optical separation of phenylglycine esters with subsequent ester hydrolysis.

According to U.S. Pat. No. 3,887,606 a DL-phenylglycine ester is treated with (+) tartaric acid in the presence of a mixture of solvents of different polarities, one of which is an alkanol having from 1 to 4 carbon atoms, and the (+) hemitartrate of the D-phenylglycine ester is selectively crystallized. Yields of 66 to 83% are indicated for the optical separation and of 60 to 75% for the subsequent hydrolysis to obtain the phenylglycidine, so that the transformation of the racemic ester into the optically active acid is in the range of from 40 to 60%.

U.S. Pat. No. 3,976,680 relates to a process for the manufacture of an ester of an enantiomer of an α-aminoacetic acid in the form of a salt with an optically active acid, wherein an ester of the opposite enantiomer of the α-amino acid is reacted with the specified optically active acid and an aldehyde or ketone, whereby the ester of the desired enantiomer separates in the form of the salt. In this manner the DL ester can be reacted, in the presence of L(+) tartaric acid, with benzaldehyde or acetone in ethanol or methanol as solvent whereby the D-phenylglycine ester is obtained as hemitartrate salt. The yields obtained are in part over 90%. For the subsequent stage of the ester hydrolysis a yield of 90% is likewise indicated.

In both processes it should be taken into consideration that in the hydrolysis the danger of an ester racemation does exist. Moreover, esterifications and ester hydrolysis are additional reactions using as starting compound the synthesized DL-C-phenylglycine; these reactions involve losses in yield.

(3) The optical separation of 2-amino-2-phenylacetonitrile and subsequent hydrolysis of the nitrile.

The racemate separation of DL-2-amino-2-phenylacetonitrile with L(+)tartaric acid has been known since 1932. H. Reihlen et al. carried out a series of investigations about the configuration of derivatives of 2-amino-2-phenylacetic acid. They crystallized the diasteromeric D(+)-2-amino-2-phenylacetonitrile-L(+)-hydrogenotartrate by fractionation from methanol and found specific rotation of the salt of $[\alpha]_D$ of 41.1° ($H_2O$).

When the mother liquid was concentrated it turned red and became smeary. From the indicated amounts a yield of 32% of the theory can be calculated, relative to the racemic nitrile (cf. Liebigs Ann. d. Chemie 534, page 247 (1938).

In 1966 D. G. Neilson and D. F. Ewing continued these works and split the aminonitrile according to the indications of H. Reihlen. They could improve the specific rotation of the D-aminonitrile-L(+)-hydrogenotartrate to $[\alpha]_D = 45.4°$ (c=0.9; $H_2O$). A yield is not indicated. The authors of these works likewise observed a substantial decomposition in the recrystallization of the salts from methanol (J.Chem.Soc. C, page 393 (1966)).

According to Hungarian Patent 154,410 there are obtained 30% of the theory of crude hydrogenotartrate ($[\alpha]_D = +41°$-43° (c=3; $H_2O$)) from the benzene extract of a conventional Strecker reaction with L(+)-tartaric acid and additional methanol and, after recrystallization from benzene/methanol, the yield amounts to about 18% of the theory, calculated on benzaldehyde ($[\alpha]_D^{20}=44°$ (c=3; $H_2O$)). Hydrolysis of this salt in boiling 20% strength hydrochloric acid yielded D(−)-C-phenylglycine.

British Pat. No. 1,382,687 claims a process in which racemic 2-amino-2-phenylacetonitrile is reacted with optically active tartaric acid in the presence of alkanoic acids having from 2 to 8 carbon atoms to obtain the tartaric acid salt of an enantiomer of the above acetonitrile.

The subsequent stage of the nitrile hydrolysis is disclosed in British Pat. No. 1,388,341. In this process D(−)-2-amino-2-(p-hydroxyphenyl)-acetonitrile-L(+)hemitartrate is subjected to an acid hydrolysis and the corresponding aminoacetic acid is obtained.

The processes of U.S. Pat. No. Great Britain Pat. No. 3,887,606 and 1,382,687 differ from the other processes proceeding via fractional crystallization of the salts in that the pair of diastereomers is transformed into only one diastereomeric salt with a suitable auxiliary.

This process which includes simultaneously racemization and separation into an optical isomer is called asymmetrical transformation of second order (cf. E. E. Turner, Quart. Rev. 1947/1, pages 299 et seq.).

The disadvantages of the aforesaid processes of the state of the art reside in the low yields and in the use of partly very expensive auxiliaries, some of which can only be used with considerable expenditure due to the unpleasant odor.

It is, therefore, the object of the present invention to provide a process for the manufacture of optically active 2-aminophenylacetic acid using cheap auxiliaries that are easy to handle, and which is easy to carry out and gives a high yield of the desired final product.

Surprisingly, it has been found that alkanols and/or ketones bring about an asymmetrical transformation of DL-aminophenylacetonitrile hydrogenotartrate salt.

This is astonishing since in the aforesaid prior attempts to separate the diastereomers of the salt in methanol substantial decomposition has been observed.

Hence, the aforesaid objective is achieved by a process for the manufacture of optically active, optionally substituted 2-amino-2-phenylacetic acid of the formula I

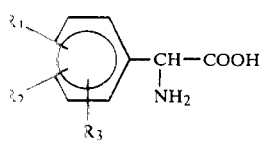

(I)

in which $R_1$, $R_2$ and $R_3$, which are identical or different, denote hydrogen, halogen, hydroxy, alkyl, acyl, or alkoxy, by asymmetrical transformation of a corresponding DL-aminophenylacetonitrile with L(+)-tartaric acid, which comprises reacting DL-2-amino-2-phenyl-acetonitrile of the formula II

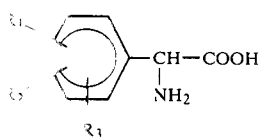

(II)

in which $R_1$, $R_2$ and $R_3$ have the above meaning, with approximately equimolar amounts of L(+)-tartaric acid in the presence of at least one alkanol having from 1 to 5 carbon atoms and/or at least one carbonyl compound at a temperature of from 0° to 50° C., bringing about transformation by stirring the mixture for 2 to 120 hours at the indicated temperature, separating the crystallized transformation product, hydrolyzing same by a treatment with an acid and isolating the optically active 2-amino-2-phenylacetic acid formed.

Suitable carbonyl compounds are aliphatic aldehydes, aromatic aldehydes, dialkyl-ketones, cycloaliphatic ketones, arylalkyl-ketones and diaryl-ketones.

The lower alcohols are preferably used in the form of mixtures with one another, for example methanol/ethanol, or they are diluted with other solvents such as aromatic hydrocarbons, aliphatic hydrocarbons, chlorinated hydrocarbons, ethers and esters.

It proved also advantageous to use alkanol/ketone mixtures for the transformation. Lower ketones such as acetone or methylethyl-ketone may, however, also be used individually.

The transformation with alkanols is distinctly accelerated at room temperature in the presence of ketones such as acetone, methylethylketone or acetophenone. The concentration of the ketone can vary in the range of from 1% by volume to more than 50% by volume. It is preferred to use equimolar amounts of ketone.

To obtain a favorable yield (over 50% of the theory, calculated on DL-α-aminonitrile derivative) the amount of solvent used should be kept as low as possible. It is necessary however, that the suspension of the α-aminonitrile-hemitartrate salt remains stirrable to ensure a uniform and complete transformation.

Depending on the type of solvent or on the composition of the solvent mixture of alkanol and/or carbonyl compound, of alkanol and inert diluent, of carbonyl compound and inert diluent, or of alkanol, carbonyl compound and inert diluent, 0.2 to 1 liter, preferably 0.4 to 0.5 liter, of solvent or solvent mixture are used for each mol of DL-2-amino-2-phenylacetonitrile of the formula II.

With the use of benzaldehyde and acetaldehyde, i.e. the lowest members of the homologous series, in alkanols the formation of by-products was observed, but this fact does not restrict the general efficacy of the claimed process.

The transformation is carried out at 0° to 50° C. over a period of from 2 to 120 hours. In contradistinction to the transformation in alkane-carboxylic acids, a complete exclusion of water is not necessary. In each individual case the exact conditions can be determined empirically by variation of temperature, time, composition of the solvent mixture used and salt concentration.

In general, L(+) tartaric acid is suspended or dissolved at room temperature (20° C.) in the respective solvent and the solid aminonitrile is then added. According to the solvent or solvent mixture used and the temperature chosen, the reaction mixture is stirred for a period within the indicated limits in a closed vessel, optionally cooled and filtered. The salt is washed with a solvent mixture as used for the transformation, or with a diluent, dried and hydrolyzed according to a known method.

The tarataric acid can be used in equimolar amounts or in an amount inferior to the stoichiometric amount. The substituted aminonitrile can be dosed also in dissolved form.

According to a special variant of the process of the invention, the DL-aminonitrile-L-hydrogenotartrate salt is prepared in methanol and the solvent is then removed by evaporation. When this pre-treated salt having a specific rotation of $[\alpha]_D = 19°-23°$ (H$_2$O) is then used for the transformation in higher alkanols, the reaction periods are shortened.

The transformation in the solvents or solvent mixtures according to the invention exclusively leads to optionally substitute D(+)-2-amino-2-phenylacetonitrile-L(+)-hydrogenotartrates which are hydrolyzed in mineral acids, preferably in 20% strength hydrochloric acid, and then yield D(−)-phenylglycines.

The following examples illustrate the invention, but they are not intended to limit it.

EXAMPLE 1

13.2 g (0.1 mol) of solid DL-2-amino-2-phenylacetonitrile were added while stirring to a solution of 15.0 g (0.1 mol) of L(+)-tartaric acid in 50 ml of methanol. The suspension formed was stirred for 8 hours at 30° C. and then allowed to cool from 30° C. to about 20° C. while stirring was continued for 14 hours.

Finally the reaction mixture was cooled to 10° C. over a period of 2 hours, filtered off with suction and washed with 20 ml of methanol. The salt was dried at about 50° C. 22.6 g (0.08 mol) of D(+)-aminophenylacetonitrile-L(+)-hydrogenotartrate were obtained corresponding to a yield of 80% of the theory, calculated on DL-aminophenylacetonitrile.

$[\alpha]_D^{20} = 44.1°$ (c=2; H$_2$O)

EXAMPLE 2

While thoroughly stirring, 12.2 g (0.1 mol) of DL-2-amino-2-phenylacetonitrile were added to a suspension of 15.0 g (0.1 mol) of L(+)-tartaric acid in a solvent mixture of 25 ml of methanol and 20 ml of dichloroethane. The suspension was stirred for 24 hours at room temperature, filtered off with suction, the salt was washed with 25 ml of methanol/dichloroethane (1:1) and dried at about 50° C. 23.8 g (0.0844 mol) of D(+)-aminophenylacetonitrile-L(+)-hydrogenotartrate, corresponding to a yield of 84.4% of the theory, calculated on the DL-aminophenylacetonitrile used, where obtained.

$[\alpha]_D^{20} = 43.5°$ (c=2; H$_2$O)

EXAMPLE 3

13.2 g (0.1 mol) of solid DL-2-amino-2-phenylacetonitrile were added while stirring to 15 g (0.1 mol) of L(+)-tartaric acid i 60 ml of absolute ethanol and the suspension formed was stirred for 52 hours at about 20° C. The precipitate was filtered off with suction, washed with 30 ml of toluene and dried at about 50° C. 23 g (0.0816 mol) of D(+)-2-amino-2-phenylacetonitrile-L-(+)-hydrogenotartrate were obtained, corresponding to a yield of 81.6% of the theory, calculated on racemic aminonitrile.

$[\alpha]_D^{20} = +43°$ (c=2; H$_2$O)

EXAMPLE 4

150 g (1 mol) of L(+)-tartaric acid were suspended in a solvent mixture consisting of 300 ml of ethanol and 90 ml of methylethylketone. Next, 132 g (1 mol) of DL-2-amino-2-phenylacetonitrile were added and the mixture was stirred at room temperature for 23 hours. The suspension of the D-aminonitrile-L-hydrogenotartrate salt was filtered off with suction, washed with 50 ml of ethanol/methylethylketone (1:2 vv) and dried at 50° C. 243 g (0.862 mol) of the L(+)-hydrogenotartrate of D(+)-aminophenylacetonitrile were obtained, corresponding to a yield of 86.2% of the theory, calculated on the DL-2-amino-2-phenylacetonitrile used.

$[\alpha]_D^{20} = +44.5°$ (c=2; H$_2$O)

EXAMPLE 5

A suspension of 28.2 g (0.1 mol) of DL-aminophenylacetonitrile-L(+)-hydrogenotartrate ($[\alpha]_D = +19.9°$ (H$_2$O)) in 80 ml of n-propanol was stirred for 120 hours at 20° C.

24.6 g (0.872 mol) of the L-hydrogenotartrate salt with D(+)-aminophenylacetonitrile were obtained, corresponding to a yield of 87.2% calculated on the racemic aminonitrile.

$[\alpha]_D^{20} = 43.6°$ (c=2; H$_2$O).

EXAMPLE 6

7.4 g (0.05 mol) of L(+)-tartaric acid were added while stirring to a solution of 8.0 g (0.05 mol) of DL-2-amino-2-(p-methoxyphenyl)-acetonitrile in 40 ml of methylethylketone and the suspension was stirred for 72 hours at room temperature. The crystals were then separated, washed with 5 ml of methanol/toluene (1:2) and dried at 50° C. The yield amounted to 14.65 g (95.1% of the theory) of D(+)-2-amino-2-(p-methoxyphenyl)-acetonitrile-L-(+)-hemitartrate having a specific rotation of $[\alpha]_D^{20} = +45°$ (c=1; H$_2$O).

EXAMPLE 7

D(+)-2-amino-2-phenylacetonitrile-L(+)-hydrogenotartrate ($[\alpha]_D^{20} = +43°$ (c=2; H$_2$O) obtained according to Examples 1 to 4 was hydrolyzed in aqueous hydrochloric acid of 20% strength as follows:

90.9 g (0.322 mol) of D(+)-aminophenylacetonitrile-L(+)-hydrogenotartrate were added to 376 g of boiling hydrochloric acid of 20% strength and refluxed for 45 minutes. The mixture was then stirred for 30 minutes at 80° C. together with 2 g of active carbon and the solution was filtered at a temperature above 50° C. While externally cooling with ice, the filtrate was adjusted to pH 7 at 50° C. using about 160 g of sodium hydroxide solution of 50% strength. After 0.5 hour, the precipitate was filtered off with suction at about 10° C., and was washed with about 250 ml of Permutit water. At the end, it was washed with 50 ml of methanol whereby colorless C-phenylglycine was obtained which was dried at 50° C.

The yield amounted to 41.2 g of D(−)-2-amino-2-phenylacetic acid (84.7% of the theory), calculated on D(+)-2-amino-2-phenylacetonitrile-L(+)-hydrogenotartrate. The melting point was 307° C.; sublimation occurred at 310° to 312° C.

$[\alpha]_D^{20} = -146.2°$ (c=1 N HCl)

What is claimed is:

1. A process for the manufacture of an optically active optionally substituted 2-amino-2-phenylacetic acid of the formula

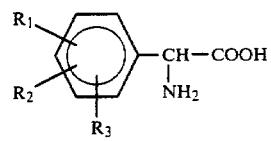

wherein R$_1$, R$_2$ and R$_3$, which are identical or not all the same, are hydrogen, halogen, hydroxy, alkyl, acyl or alkoxy, which consists essentially of reacting a DL-2-amino-2-phenyl-acetonitrile of the formula

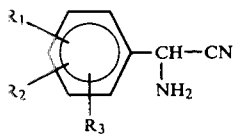

with an approximately equimolar amount of L(+)-tartaric acid in the presence of at least one alkanol of from 1 to 5 carbon atoms at a temperature of from 0° to 50° C.; stirring the reaction mixture for 2 to 120 hours at a temperature of from 0° to 50° C., thereby bringing about asymmetrical transformation; separating the crystallized transformation product; hydrolyzing same by a treatment with an acid; and isolating the optically active 2-amino-2-phenylacetic acid form.

2. The process as defined in claim 1, wherein D(−)-2-amino-2-phenylacetic acid is prepared from DL-2-amino-2-phenylacetontrile.

3. The process as defined in claim 1, wherein D(−)-2-amino-2-(4-methoxyphenyl)-acetic acid is prepared from DL-2-amino-2-(4-methoxyphenyl)-acetonitrile.

4. The process as defined in claim 1, wherein hydrochloric acid of 20% strength is used for the hydrolysis.

5. The process as defined in claim 1, wherein the alkanol is methanol.

6. The process as defined in claim 1, wherein an amount of from 0.2 to 1 liter of the alkanol is introduced for each mol of the DL-2-amino-2-phenyl-acetonitrile.

7. The process as defined in claim 6, wherein an amount of from 0.4 to 0.5 liter of the alkanol is introduced.

8. The process as defined in claim 1, wherein the DL-2-amino-2-phenyl-acetonitrile is reacted with an equimolar amount of L(+)-tartaric acid in an alkanol, and the hemitartrate salt formed as an intermediate is isolated and transformed in an alkanol of from 1 to 5 carbon atoms.

9. The process as defined in claim 1, wherein the yield of 2-amino-2-phenylacetic acid is greater than 50% calculated on the DL-2-amino-2-phenyl-acetonitrile.

* * * * *